United States Patent [19]

Wirtzfeld et al.

[11] Patent Number: 4,763,655
[45] Date of Patent: Aug. 16, 1988

[54] FREQUENCY-CONTROLLED HEART PACEMAKER

[75] Inventors: Alexander Wirtzfeld, Ingolstadt/Friedrichshofen; Karl Stangl; Roland Heinze, both of Munich, all of Fed. Rep. of Germany

[73] Assignee: Siemens Aktiengesellschaft, Berlin and Munich, Fed. Rep. of Germany

[21] Appl. No.: 62,707

[22] Filed: Jun. 16, 1987

[30] Foreign Application Priority Data

Jun. 16, 1986 [DE] Fed. Rep. of Germany ....... 3620278

[51] Int. Cl.$^4$ .............................................. A61N 1/36
[52] U.S. Cl. .............................................. 128/419 PG
[58] Field of Search .................................. 128/419 PG

[56] References Cited

U.S. PATENT DOCUMENTS

| | | | |
|---|---|---|---|
| 4,201,219 | 5/1980 | Bozal Gonzalez | 128/419 PG |
| 4,202,339 | 5/1980 | Wirtzfeld et al. | 128/419 PG |
| 4,399,820 | 9/1983 | Wirtzfeld et al. | 128/419 PG |
| 4,436,092 | 3/1984 | Cook et al. | 128/419 PG |
| 4,594,565 | 6/1986 | Barreras | 128/419 PG |
| 4,688,573 | 9/1987 | Alt | 128/419 PG |
| 4,716,887 | 1/1988 | Koning et al. | 128/419 PG |

*Primary Examiner*—William E. Kamm
*Assistant Examiner*—Timothy Keegan
*Attorney, Agent, or Firm*—Hill, Van Santen, Steadman & Simpson

[57] ABSTRACT

The stimulation frequency of a heart pacemaker is controlled dependent on a signal representative of the blood oxygen content of the patient. The blood oxygen dependent signal is generated by a blood oxygen sensor. A temperature sensor generates a separate signal dependent on blood temperature. The blood oxygen and blood temperature signals are combined such that the blood oxygen signal is lowered, i.e., the value thereof is reduced, in ranges of higher physical load indicated by an increase in the temperature dependent signal. The combined signal is used to control the stimulation frequency of a heart pacemaker so that the stimulation frequency is increased, if blood oxygen saturation is decreasing and/or blood temperature is increasing.

8 Claims, 2 Drawing Sheets

FREQUENCY-CONTROLLED HEART PACEMAKER

BACKGROUND OF THE INVENTION

1. Field of the Invention

The present invention is directed to a frequency-controlled heart pacemaker, and in particular to a heart pacemaker wherein the stimulation frequency is controlled dependent on a measurement of the blood oxygen saturation of the patient.

2. Description of the Prior Art

Controlling the stimulation frequency of a heart pacemaker based on a measurement of the blood oxygen saturation of the patient is known, for example, from German OS No. 34 22 913.

It is also known that as the body enters into the anaerobic metabolic condition given higher stress, changes in the blood oxygen saturation asymptotically approach a zero value. This can cause conventional pacemaker control systems, making use of blood oxygen saturation as a factor in setting the stimulation frequency, to operate imprecisely when the body is in a higher stress condition.

SUMMARY OF THE INVENTION

It is an object of the present invention to provide a frequency-controlled heart pacemaker wherein control of the stimulation frequency is at least in part based upon a measurement of the blood oxygen saturation of the patient, and wherein control of the stimulation frequency is not influenced by a reduction in the blood oxygen saturation if the patient is physically under higher load conditions.

The above object is achieved in accordance with the principles of the present invention in a heart pacemaker having a blood oxygen sensor which generates a signal corresponding to the blood oxygen saturation of a patient, a temperature sensor which generates a signal dependent on the blood temperature of the patient, and means for combining the blood oxygen signal and the temperature signal such that the values of the blood oxygen signal are reduced in ranges of higher load, such load being indicated by the value of the temperature dependent signal. The combined signal is supplied to a frequency control unit for a pulse generator in the heart pacemaker, so that the stimulation frequency is controlled by the combined signal of oxygen saturation and temperature.

The invention makes use of the fact that the temperature in venous blood increases when the body is under load. If both the temperature and the blood oxygen level of a patient are measured, and respective signals generated corresponding to the blood oxygen and to the temperature, the temperature signal will behave opposite to the blood oxygen signal. The blood oxygen signal, which decreases under higher load, is decreased further in accordance with the principles of the present invention by combination with the temperature signal, which increases under higher load. A control signal for the frequency control unit of a heart pacemaker is thus obtained which is more exact than the control signal based solely on blood oxygen level in conventional frequency-controlled heart pacemakers.

DESCRIPTION OF THE PREFERRED EMBODIMENTS

Figure 1:
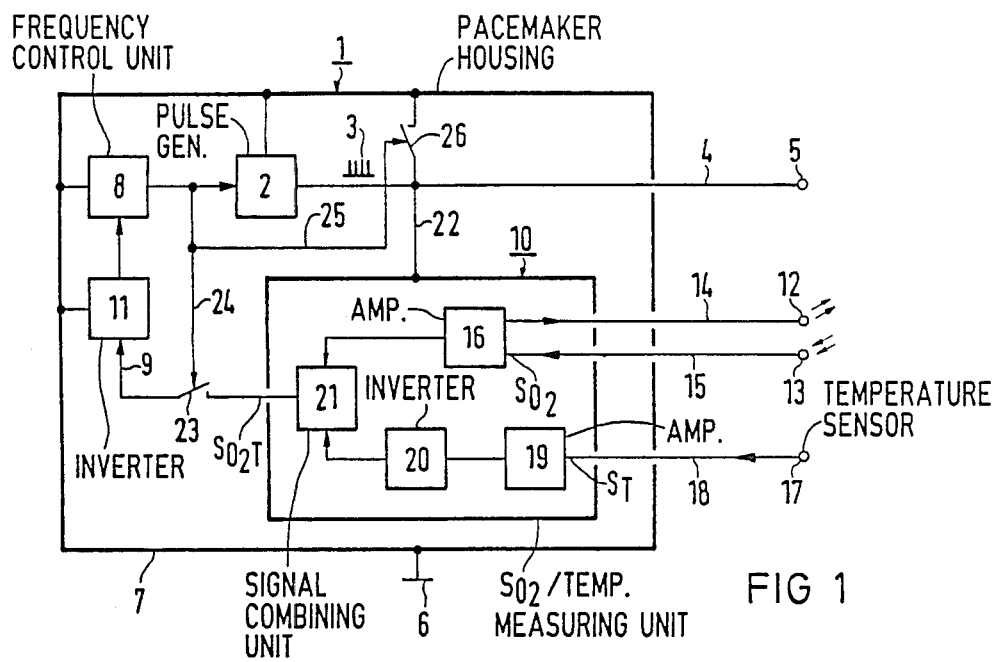
FIG. 1 is a schematic block diagram of a frequency-controlled heart pacemaker constructed in accordance with the principles of the present invention.

A frequency-controlled heart pacemaker constructed in accordance with the principles of the present invention is generally referenced at 1 in FIG. 1. The pacemaker includes a pulse generator 2 which generates stimulation pulses 3, which can be conducted to a stimulation electrode 5 via a stimulation catheter 4. The heart pacemaker 1 has a passive electrode 6, which may be the conductive (for example, metallic) housing 7 of the heart pacemaker 1.

The pacemaker 1 also includes a frequency control unit 8 which sets a desired stimulation frequency at the pulse generator 2.

The frequency control unit 8 is inversely driven by the output signal $S_{O_2}T$ from a blood oxygen/temperature sensing unit 10. The signal is supplied to the frequency control unit 8 on a control line 9. An inverter 11 is connected in the control line 9 between the frequency control unit 8 and the measuring unit 10. As the output signal $S_{O_2}T$ becomes larger, therefore, the stimulation frequency at the pulse generator 2 will be decreased. As the output signal $S_{O_2}T$ decreases, the stimulation frequency is correspondingly increased.

The blood oxygen/temperature measuring unit 10 includes a light transmitter 12 and a light receiver 13 for measuring the blood oxygen level of the patient. The light transmitter 12 is connected via a line 14 to an amplifier 16, and the light receiver 13 is connected to the amplifier 16 via a line 15. The measuring unit 10 further includes a temperature sensor 17 connected via a line 18 to an amplifier 19. The temperature sensor 17 generates a temperature signal $S_T$. The amplifier 19 is followed by an inverter 20. The output signal (inverted temperature signal) of the inverter 20 is supplied to a signal combining unit 21 together with the output signal (signal dependent on blood oxygen) of the amplifier 16. In the signal combining unit 21, the inverted temperature signal is superimposed on the blood oxygen signal such that the blood oxygen is lowered in higher load ranges. The temperature signal $S_T$ has a higher value in these ranges, and by inverting that signal in the inverter 20, the output of the inverter 20 has a lower value in those regions, which is used to decrease the blood oxygen signal in those ranges, such as by adding the inverted signal thereto.

During the time of a blood oxygen/temperature measurement (which is made intermittently between successive stimulation pulses), the stimulation catheter 4 functions as the second supply line for the measuring unit 10. For this purpose, the measuring unit 10 is connected to the line from the stimulation catheter 4 by a connecting line 22. For the purpose of making a blood oxygen/temperature measurement, a switch 23, arranged in the control line 9 between the measuring unit 10 and the inverter 11, is controlled by the output signal of the frequency control unit 8 via a line 24. The switch 23 is closed between two successive stimulation pulses 3. Simultaneously a further switch 26 is closed via the branch line 25, so that the stimulation electrode 5 is connected to ground via the stimulation catheter 4. Is is thereby assured that no test current can flow through the stimulation circuit.

Figure 2:
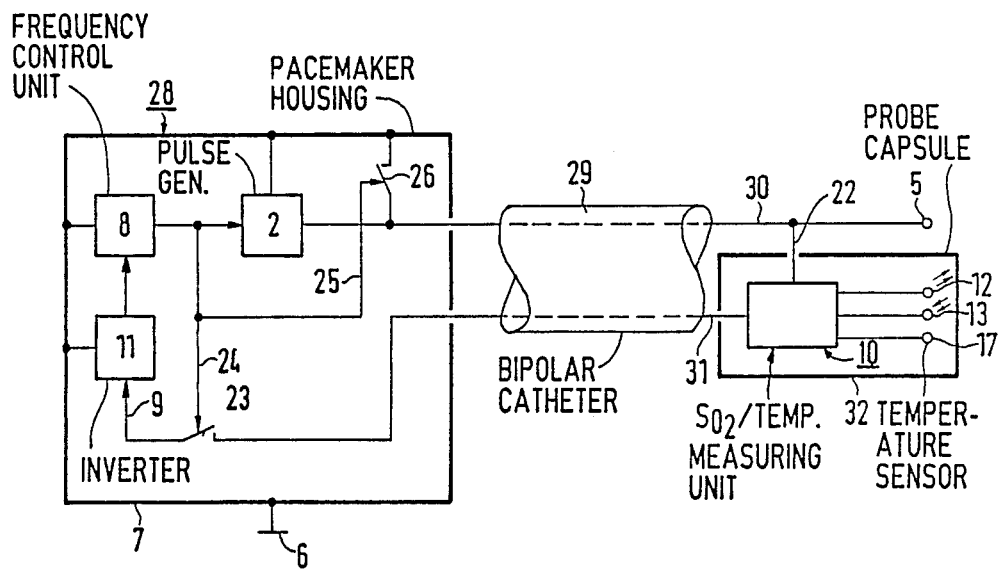
FIG. 2 is a schematic block diagram of a further embodiment of a frequency-controlled heart pacemaker constructed in accordance with the principles of the present invention.

Another embodiment of a frequency-controlled heart pacemaker constructed in accordance with the principles of the present invention is shown in FIG. 2, the pacemaker being generally referenced at 28. The embodiment of FIG. 2 differs from the embodiment of FIG. 1 in that the blood oxygen/temperature measuring unit 10 is disposed outside of the housing 7 of the heart pacemaker. The measuring unit 10 is preferably disposed in the stimulation catheter a few centimeters behind the stimulation electrode 5. To this end, the stimulation catheter is a bipolar catheter, referenced at 29 and indicated with dashed lines in FIG. 2. The first lead of the bipolar catheter 29, to which the stimulation electrode 5 is connected, is referenced 30 in FIG. 2. The second lead 31 is connected to a probe capsule 32, in which the blood oxygen/temperature measuring unit 10 is disposed together with the light transmitter 12, the light receiver 13 and the temperature sensor 17. The function of the system shown in FIG. 2 is the same as that described in FIG. 1.

Figure 3:
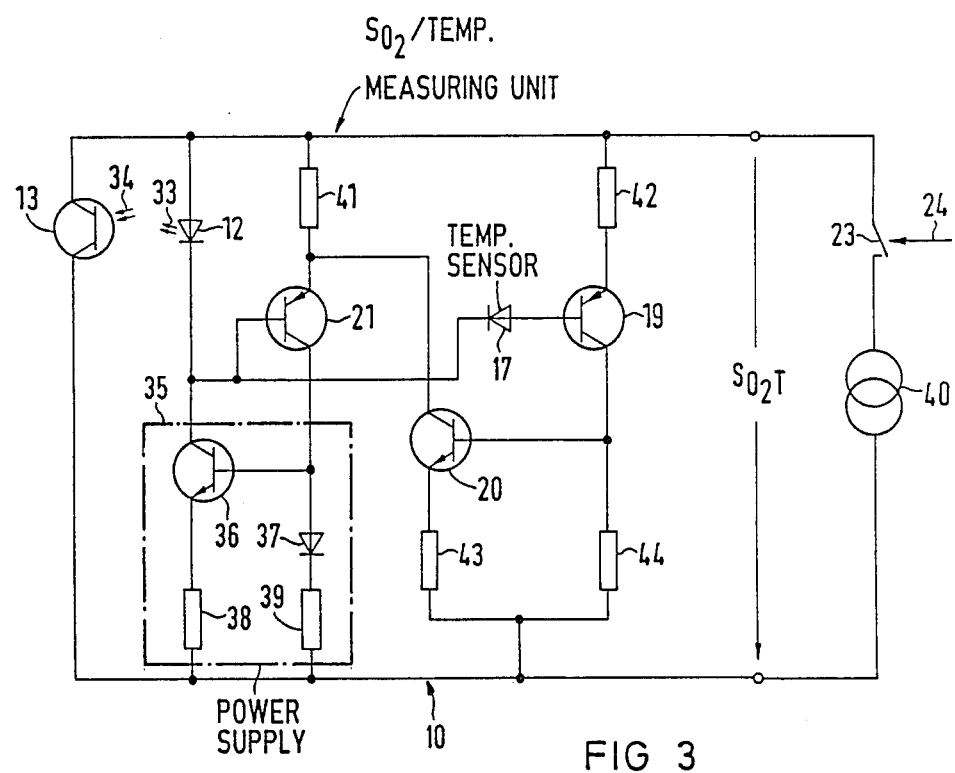
FIG. 3 is a circuit diagram of the blood oxygen/temperature measuring unit of the pacemaker of FIGS. 1 or 2.

A circuit diagram for the blood oxygen/temperature measuring unit 10 of FIGS. 1 or 2 is shown in FIG. 3. The light transmitter 12 is shown in FIG. 3 as a light-emitting diode. The light receiver 13 is a phototransistor. Light emitted into the blood by the light transmitter 12 is referenced 33, and light received by the light receiver 13 after reflection by the blood is referenced 34. A temperature-dependent semiconductor functions as the temperature sensor 17. A transistor is employed as the amplifier 19 for the temperature signal. The inverter 20 is also formed by a transistor. The inverted output signal proceeds from the collector of the transistor 20 to the collector of a current control transistor, which forms the signal combining unit 21. The current control transistor modifies the output of the power supply 35 for the light transmitter 12 in the sense that a rising temperature causes a reduced power flow through the light transmitter 12, and a decreasing oxygen content in the blood is simulated. The power supply 35 includes a transistor 36, a stabilizing diode 37 and ohmic resistors 38 and 39.

A constant current source 40 supplies the entire system of FIG. 3. Components 41 through 44 are ohmic resistors of suitable values.

Although modifications and changes may be suggested by those skilled in the art it is the intention of the inventors to embody within the patent warranted hereon all changes and modifications as reasonably and properly come within the scope of their contribution to the art.

We claim as our invention:

1. A frequency-controlled pacemaker for stimulating the heart of a patient comprising:
    means for generating stimulation pulses to the heart at a stimulation frequency;
    means for controlling the stimulation frequency of said means for generating stimulation pulses;
    means for obtaining a signal corresponding to the blood oxygen level of said patient which has lower values when said patient is under load;
    means for obtaining a signal corresponding to the blood temperature of said patient which has higher values when said patient is under load;
    means for combining said signal corresponding to the blood oxygen level and said signal corresponding to the temperature, such that said signal corresponding to the blood oxygen level is decreased in ranges of said signal corresponding to the blood temperature having higher values; and
    means for supplying the combined signal to said means for controlling the frequency.

2. A pacemaker as claimed in claim 1, wherein said means for combining includes means for inverting said signal corresponding to the blood temperature and means for adding the inverted signal corresponding to the blood temperature to the signal corresponding to the blood oxygen level.

3. A pacemaker as claimed in claim 1, further comprising a stimulation electrode having a stimulation catheter, and wherein said means for obtaining said signal corresponding to the blood oxygen level and said means for obtaining said signal corresponding to the blood temperature are disposed in said stimulation catheter.

4. A pacemaker as claimed in claim 3, further comprising a probe capsule in said stimulation catheter in which said means for obtaining said signal corresponding to the blood oxygen level and said signal corresponding to the blood temperature are disposed.

5. A pacemaker as claimed in claim 1, wherein said means for obtaining a signal corresponding to the blood oxygen level includes a light transmitter disposed for emitting light onto the blood, a light receiver disposed for receiving light from said light transmitter reflected by the blood and means for supplying operating current to said light transmitter, and wherein said means for combining includes means connected to said means for obtaining said signal corresponding to the blood temperature for lowering said operating current given rising temperature.

6. A method for operating a heart pacemaker in a patient comprising:
    generating stimulation pulses to the heart of said patient at a stimulation frequency;
    obtaining a signal corresponding to the blood oxygen level of said patient;
    obtaining a signal corresponding to the blood temperature of said patient;
    combining the signal corresponding to the blood oxygen level and the signal corresponding to the blood temperature such that said signal corresponding to the blood oxygen is decreased in ranges of said signal corresponding to the blood temperature having higher values; and
    using the combined signal to control the stimulation frequency of said pacemaker.

7. A method as claimed in claim 6, wherein the step of combining is further defined by the steps of:
    inverting said signal corresponding to the blood temperature;
    adding the inverted signal corresponding to the blood temperature to the signal corresponding to the blood oxygen level; and
    inverting the combined signal.

8. A method as claimed in claim 6, wherein the step of combining is further defined by the steps of:
    inverting said signal corresponding to the blood oxygen level; and
    adding the inverted signal corresponding to the blood oxygen level to the signal corresponding to the blood temperature.

* * * * *